United States Patent [19]
Harper

[11] Patent Number: 5,389,883
[45] Date of Patent: Feb. 14, 1995

[54] MEASUREMENT OF GAS AND WATER CONTENT IN OIL

[75] Inventor: Richard Harper, Essex, United Kingdom

[73] Assignee: GEC-Marconi Limited, Stanmore, United Kingdom

[21] Appl. No.: 121,548

[22] Filed: Sep. 16, 1993

[30] Foreign Application Priority Data

Oct. 15, 1992 [GB] United Kingdom ............... 9221650

[51] Int. Cl.⁶ ................................... G01N 22/04
[52] U.S. Cl. ......................... 324/636; 73/61.44
[58] Field of Search ............ 324/640, 634, 636, 643; 73/61.44

[56] References Cited

U.S. PATENT DOCUMENTS 5,101,163  3/1992  Agar ................... 324/640 X
5,157,339  10/1992 Scott et al. ............ 324/640
5,241,279  8/1993  Boniort et al. ......... 324/636

FOREIGN PATENT DOCUMENTS 0508854  10/1992  European Pat. Off. .
144351   6/1991   Japan .................. 324/640
2120791  12/1983  United Kingdom .

Primary Examiner—Hezron E. Williams
Assistant Examiner—Joseph W. Roskos
Attorney, Agent, or Firm—Spencer, Frank & Schneider

[57] ABSTRACT

In order to measure the relative proportions of oil, water and gas passing along a pipe, the pipe is passed through the coils of a number of coil resonators having different resonant frequencies. By measuring changes in the resonant frequencies of the coil resonators the proportions of oil, water and gas in the flow through the pipe can be calculated.

11 Claims, 3 Drawing Sheets

MEASUREMENT OF GAS AND WATER CONTENT IN OIL

FILED OF THE INVENTION

This invention relates to the measurement of the gas and water content of oil, particularly crude oil.

BACKGROUND OF THE INVENTION

Where crude oil is being pumped from the ground it is generally desirable to be able to measure its gas and water content.

In the past a number of methods of measuring the gas and water content of crude oil have been proposed. These generally fall into two types, the first being methods where a sample of the oil flow is taken and the sample is analysed and the other being so called full flow systems where the aggregate gas and water content of the entire flow is measured.

In general measurement methods involving sampling have been unpopular because the gas and water content of the oil flow is non-homogenous over time or across the width of a pipe so there is no guarantee that a sample is representative unless a homogeniser is used to homogenise the gas, oil and water in the flow. Generally speaking homogenisers are not completely effective and require power to operate them. The need for such power supply can be a considerable problem in under sea applications but the main problem with systems of this type is the difficulty of ensuring that a sample is fully representative of the gas and water content of the oil flow as a whole even when a homogeniser is used.

As a result full flow systems are preferred. One method of carrying out full flow measurement which has been proposed is the use of microwave energy. If microwave energy is passed through a mixture of water, oil and gas it is possible to deduce the proportions of the flow made up of the three constituents by measuring the attenuation of the microwave energy. This is possible because oil, water and gas have very different permitivities.

Theoretically such a calculation would be extremely simple if the flow of oil, gas and water was homogenous. However as explained above generally it is not homogenous and as a result, in practice, it has proved extremely difficult to relate the changes in permitivity measured by microwave absorption systems to the actual proportions of water and gas in the oil flow.

This invention was intended to produce a method of measurement of the gas and water content in oil overcoming these problems, at least in part.

SUMMARY OF THE INVENTION

This invention provides apparatus for measuring the relative proportions of dissimilar fluids within a pipe comprising: a plurality of coil resonators with different resonant frequencies surrounding the pipe with the pipe passing through the coils of the coil resonators; a variable frequency source of electromagnetic radiation for sending electromagnetic radiation at a plurality of different frequencies into the coil resonators, and an electromagnetic radiation sensor for measuring electromagnetic radiation emitted by each of the coil resonators.

BRIEF DESCRIPTION OF THE DRAWINGS

Apparatus embodying the invention will now be described by way of example only with reference to the accompanying diagrammatic figures in which.

DETAILED DESCRIPTION

Figure 1:
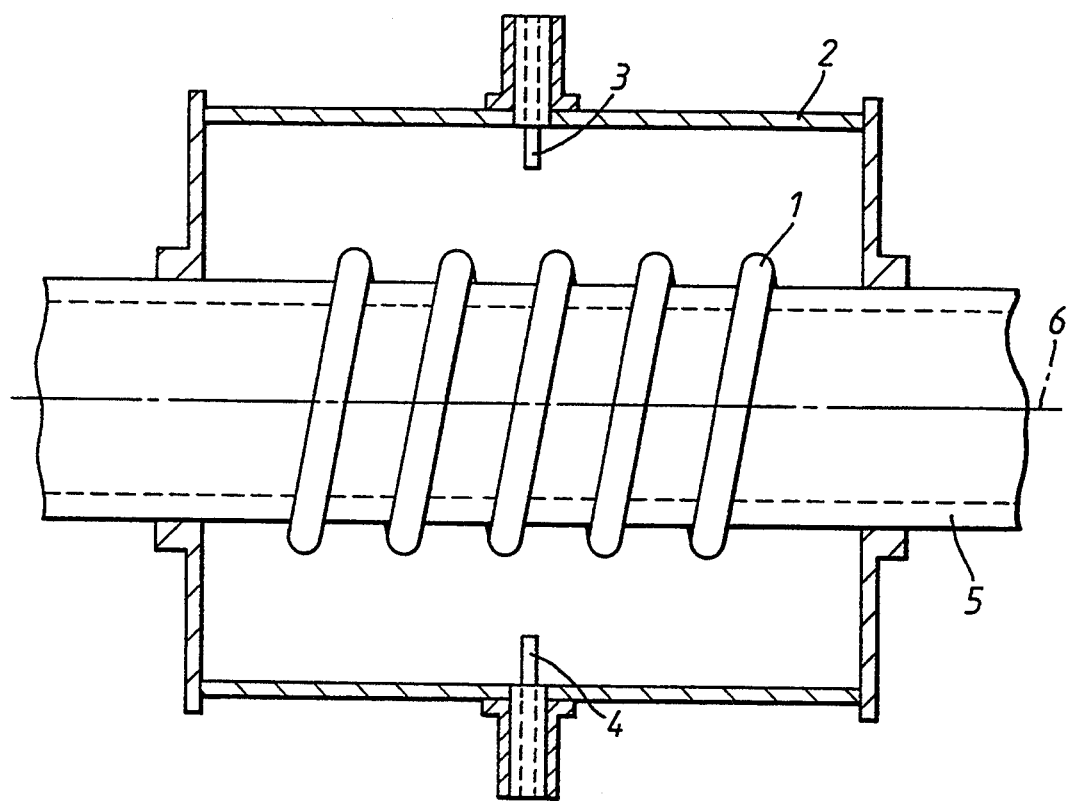
FIG. 1 shows a helical coil resonator suitable for use in apparatus for measuring the amount of oil, gas and water in a fluid flow.

Referring to FIG. 1 a helical coil resonator is shown. This comprises a conductor 1 shaped into a helix to form a helical coil having an axis 6 and contained within a conductive metal cavity 2. RF or microwave power can be input to the resonator through an input coaxial probe 3 and the resulting activity of the resonator can be sensed using an output coaxial probe 4.

The natural resonant frequency of the helical coil resonator depends on the size of the cavity 2 and the helical coil 1; as is usual in RF and microwave resonators, the larger the elements are the lower the natural resonant frequency. The natural resonant frequency is the resonant frequency with the helical coil resonator containing only air and the actual resonant frequency can be varied by the amount and dielectric constant of material within the cavity 2. If a dielectric pipe 5 is passed through apertures in the cavity 2 and through the helical coil 1 the resonant frequency of the helical coil resonator will depend on the dielectric constant and amount of any material passing through the pipe 5.

The resonant peak of the helical coil resonator for any given input power will change in both frequency and amplitude in dependence on the material within the pipe 5. The resonant frequency is affected by the dielectric constant of the material within the pipe 5 while the amplitude of the resonant peak is affected by the absorption of the material within the pipe. Both the dielectric constant and the absorption of the material are given by its complex permitivity, so a helical coil resonator is sensitive to complex permitivity.

Figure 2:
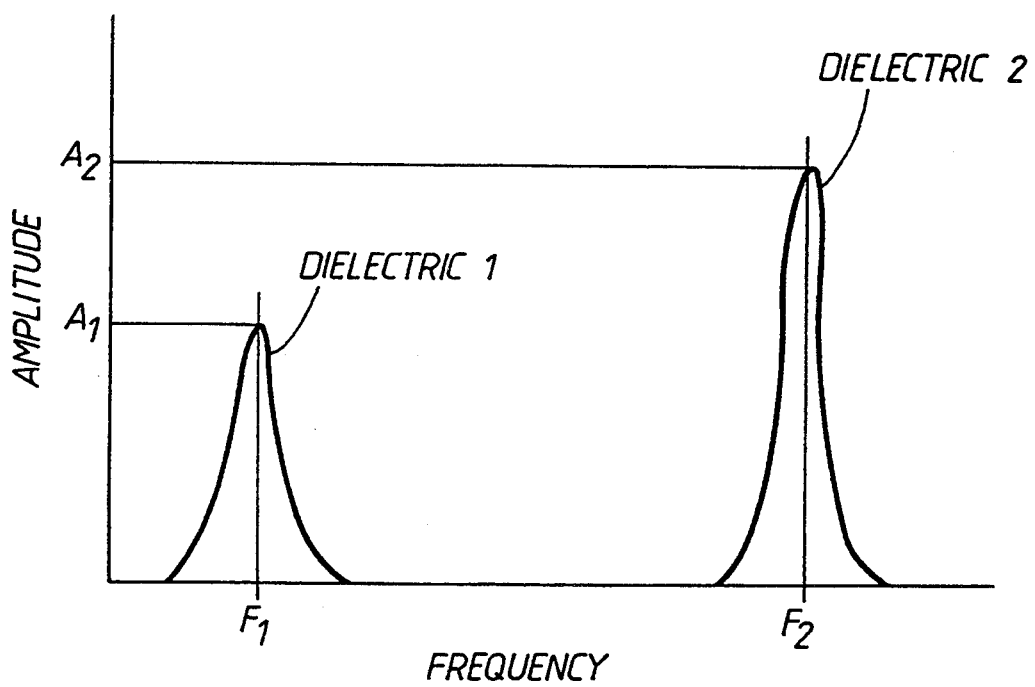
FIG. 2 shows the resonant curve characteristics of a helical coil resonator.

Referring to FIG. 2, an example of the frequency and amplitudes of the resonance peak of a helical coil resonator containing the same amounts of two dielectrics having different complex permitivities is shown.

Where the fluid passing through the pipe 5 is a mixture of oil, water and gas the amount of material within the pipe 5, in terms of volume, is constant since the pipe 5 is always full of something. However it is necessary to measure the complex permitivity of the mixture at at least two different frequencies in order to find the relative proportions of the three constituents.

A system of this type is particularly sensitive to the amount of water in the fluid flow because water has a very different complex permitivity to that of oil because of water's high dielectric constant and strong microwave absorption. However since there are three different materials, oil, water and gas, which may be constituents in the fluid flow through the pipe 5, even though they have different complex permitivities it is not possible to unambiguously calculate their relative proportions from the frequency and amplitude of resonation of a single helical coil resonator. However by employing two different helical coil resonators having different sizes and thus different natural resonant frequencies it is possible to calculate the relative portions of oil, water and gas in the fluid that flows through the pipe 5 because the complex permitivity of water is variable with frequency. The ratio of the imaginary and real parts of the complex permitivity of water, that is the ratio of the dielectric constant to absorption, the so called loss tangent, progressively increases with frequency up to approximately 20 GHz. As a result, by measuring the frequency and amplitude of the resonant peaks of two different helical coil resonators of different sizes it is possible to calculate the relative proportions of oil, water and gas in the fluid flow.

There is one drawback with such a system, which is that the resonant frequency of the helical coil resonator is more sensitive to the properties of material in the vicinity of the coil 1 itself than it is to the properties of material elsewhere within the cavity 2 because the strength of the electric fields generated by the coil 1 are stronger there.

As a result, if the pipe 5 is filled with a non-homogenous flow of oil, water and gas the resonator will be more sensitive to the proportions of oil, water and gas in the flow close to the walls of the pipe 5, and thus close to the helical coil 1, than it would be to the proportions of oil, water and gas in the flow near to the centre of the pipe 5. Since the relative proportions of oil, water and gas close to the walls of the pipes may be different to their overall proportions in the flow this could give incorrect results.

This problem can be overcome in several ways, the first being to homogenise the oil, water and gas flow before it passes through the pipe 5. This would be satisfactory if complete homogenisation of the oil, water and gas in the flow could be guaranteed, but as explained above it cannot, and in any case this procedure would still have the disadvantage of requiring a power supply to drive the homogeniser.

A second method of overcoming this problem is to constrain the fluid flow to a relatively small region about the central axis 6 of the helical coil 1. In this region the electrical fields generated by the helical coil are linear and as a result inhomgenity of the fluid flow in this region will not cause a problem. This is because the different parts of the fluid flow having different complex permitivities will all be given equal weight in their effect on the resonance peak of the resonator.

Clearly there is a disadvantage associated with this system, which is that the helical coil 1 and cavity 2 must be very large relative to the internal diameter of the dielectric pipe 5. Although this might not be a disadvantage in some situations, in attempting to measure the full flow from an oil well, where the internal diameter of the pipe 5 would have to be quite large, the bulk of the helical coil 1 and cavity 2 could be a problem.

Figure 3:
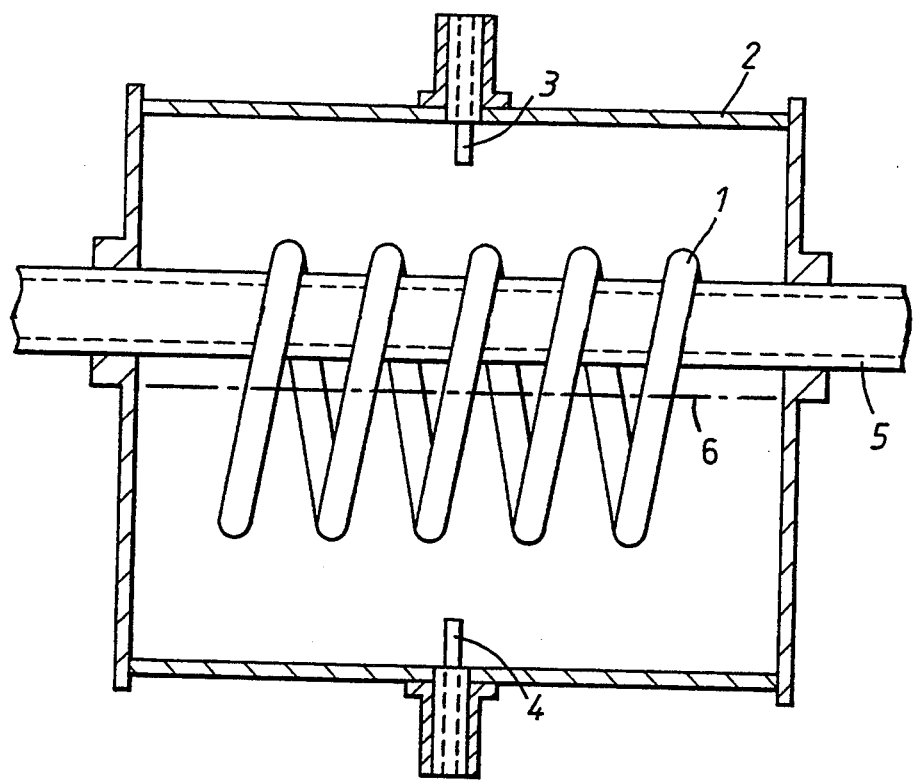
FIG. 3 shows second type of helical coil resonator suitable for use in apparatus for measuring the amount of oil, gas and water in fluid flow.

An alternative system overcoming this problem is shown in FIGS. 3 and 4 and is to use a plurality of helical coils 1 of equal size arranged around a pipe 5 so that the pipe 5 is offset from the axis 6 of the coils 1. This requires the pipe 5 to be smaller than the internal diameter of the helical coil 1 but it does not require the diameter of the pipe 5 to be as small relative to the diameter of the helical coil 1 as the system previously described. It has been found that the internal diameter of the pipe containing the fluid flow should be approximately 50% smaller than the diameter of the coil.

Referring to FIG. 4 the arrangement of the coils 1 around the pipe 5 is shown. In this case 8 coils are used but any number could be used, the number chosen being a trade off between increasing the accuracy and sensitivity of the system by increasing the number of coils 1 used and the increase in the cost and bulk of the system due to the use of more coils 1.

Figure 4A:
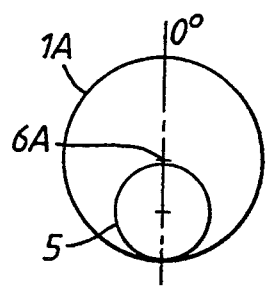
FIGS. 4A to 4H show cross sectional views of apparatus employing helical coil resonators as shown in FIG. 3.

Referring to FIG. 4A the first coil 1A is arranged so that it is adjacent to the outer wall of the pipe 5 at one point along its circumference and a line drawn through the axis 6A of the coil 1A and the axis of the pipe 5 lies at an angle of 0° relative to the pipe 5. In FIGS. 4 all of the coils 1 are shown end on as simple circles.

Figure 4B:
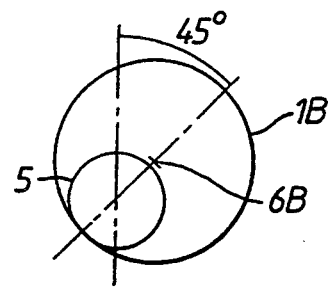

In FIG. 4B the second coil 1B is shown arranged like the coil 1A except that a line through the axis of the pipe 5 and the axis 6B of the coil 1B lies at an angle of 45° relative to the pipe 5.

Figure 4C:
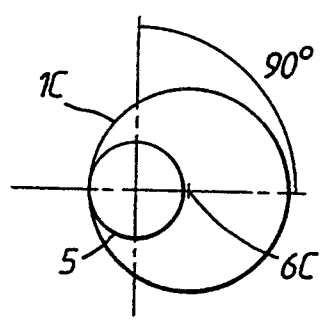
Figure 4D:
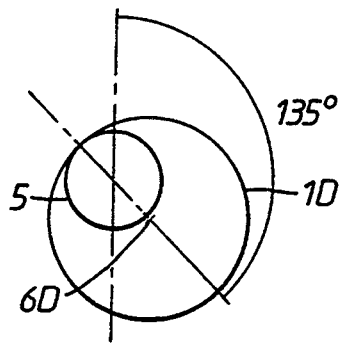
Figure 4E:
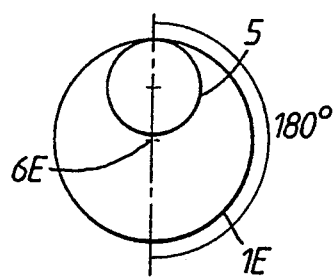
Figure 4F:
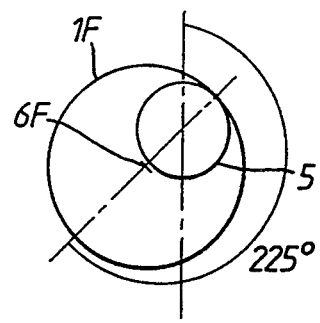
Figure 4G:
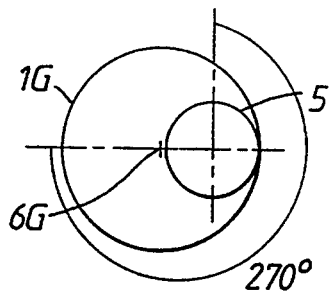
Figure 4H:
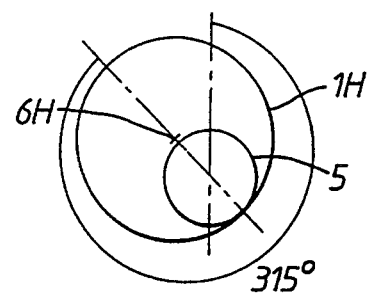

Similarly, in FIG. 4C the coil is arranged so that a line through its axis 6C and the axis of the pipe 5 is at an angle of 90° relative to the pipe 5 and the pipe 5 adjacent the coil 1C. The remaining coils 1D, 1E, 1F, 1G and 1H are similarly arranged at 45° angular intervals. As can be seen, this results in each of the coils 1A to 1H being adjacent to a separate part of the fluid flow through the pipe 5. All of the coils 1 are arranged to have the same offset distance, the offset distance being the distance between the axis 6 of the coil 1 and the axis of the pipe 5.

Due to the non-linearity of the electric fields generated by the helical coils 1 in the immediate vicinity of the helical coils 1 the resonant peak of each helical coil 1 is much more strongly influenced by the part of the fluid flow through the pipe 5 adjacent to the coil than by the parts of the flow elsewhere in the pipe 5. As a result the resonant peaks of the helical coils 1A to 1H will be mainly influenced by the part of the fluid flow adjacent each coil and since each coil is adjacent a different part of the fluid flow this will allow a coarse map of the distribution of oil, water and gas within the pipe 5 to be produced if required. More usefully, by analysing the area adjacent each coil for its mixture content and then summing over all the areas, the volumetric components of oil, water and gas for the full flow can be found.

Figure 5:
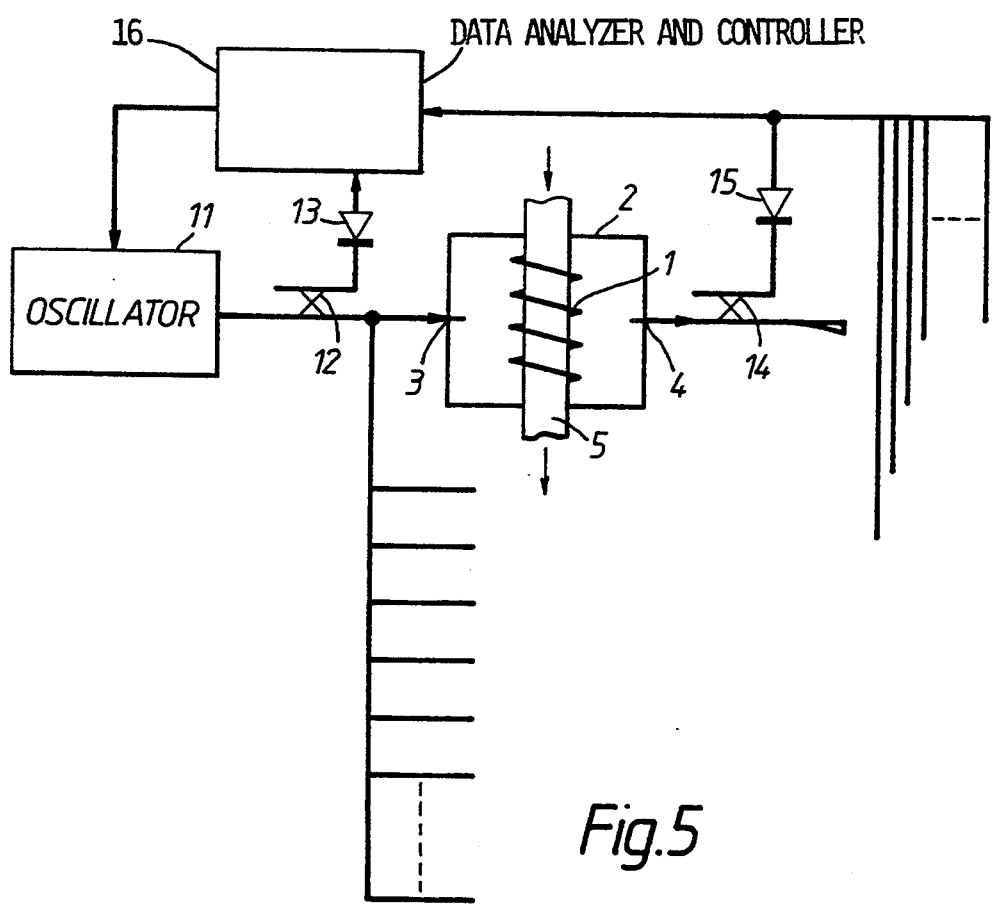
FIG. 5 shows an overall view of the apparatus of FIGS. 3 and 4, similar parts having the same reference numerals throughout.

Referring to FIG. 5 a system employing this technique is shown. This comprises a microwave oscillator 11 having its output variable across a range of frequencies and arranged to supply microwave radiation to a coil resonator 1. A coupler 12 takes a portion of the input power to the resonator 1 and supplies it to a microwave detector 13 which measures it. The output from the helical coil resonator 1 is picked up by a second coupler 14 and supplied to a second microwave detector 15.

In operation a mixture of oil, water and gas passes through the pipe 5 which passes through the coil resonator 1. A data analyser and controller 16 varies the frequency of the microwave oscillator 11 and plots the output voltages derived from the output signal from the coil resonator 1 by the second microwave detector 15. Simultaneously the controller 16 uses the voltage generated by the first microwave detector 13 corresponding to the input power to the helical coil resonator to provide information for a feedback loop to ensure that the output power of the microwave oscillator 11 and thus the input power to the helical coil resonator remains constant.

The output power of the helical coil resonator is plotted against the input frequency to produce the resonant peak for the helical coil resonator.

Sixteen separate helical coil resonators are used, all supplied with a microwave signal simultaneously by the microwave oscillator 11. The 16 helical coil resonators each have a respective second coupler 14 and second microwave detector 15 to produce a voltage representative of their respective output power. The helical coil resonators are arranged in two groups of 8 arranged around the pipe 5 with all of the coil resonators in each group of 8 helical coil resonators having same size and being arranged to resonate at the same natural frequency and the helical coil resonators of the different groups of 8 helical coil resonators being differently sized to resonate at a different natural frequency. Each group of 8 helical coils resonators is arranged offset at different angles around the pipe 5 as described above with reference to FIG. 4.

The analyser and controller 16 is thus provided with resonance peaks from 8 positions around the pipe 15 for two different natural resonance frequencies and uses these resonance peaks to calculate the relative proportions of the oil, water and gas in the fluid passing through the pipe 5.

In an alternative construction the power levels of the radiation emitted by the microwave oscillator 11 need not be kept constant. Instead the power levels of the microwave signals at the two couplers 12 and 14 can be compared as the microwave oscillator 11 is swept through a range of frequencies in order to obtain the position and amplitude of the resonance peak.

If further detail about the proportions of oil, water and gas at different points the flow through the pipe 5 was required this could be provided by additional coils at different offset distances from the pipe 5.

These techniques could be used to analyse the flow of any dissimilar fluids through a pipe provided the fluids have different complex permitivities but it is particularly suitable for measuring a proportion of gas and water in crude oil.

A system as described will only provide information on the relative proportions of gas oil and water in the pipe. In order to determine the absolute volumes of the three fluids passing through the pipe, additional apparatus to determine the rate of flow of the fluid within the pipe would be needed. Such apparatus is well known in itself and need not be described in detail here.

The microwave oscillator could be replaced by an R.F. oscillator; helical coil resonators work just as well at R.F. frequencies (500 MHz to 1 GHz) as they do at microwave frequencies (1 GHz to 20 GHz).

I claim:

1. Apparatus for measuring the relative proportions of dissimilar fluids within a pipe, comprising: a plurality of coil resonators with different resonant frequencies surrounding the pipe with the pipe passing through the coils of the coil resonators, the coil resonators being split into a plurality of groups each comprising a plurality of coil resonators having the same natural resonant frequency, the resonators of the different groups having different natural resonant frequencies; a variable frequency source of electromagnetic radiation for sending electromagnetic radiation at a plurality of different frequencies into the coil resonators; and an electromagnetic radiation sensor for measuring electromagnetic radiation emitted by each of the coil resonators.

2. Apparatus as claimed in claim 1, in which the coil resonators are all offset from the pipe, all of the coil resonators in each group being offset by the same amount and the coil resonators of each group being spaced at equal angular intervals around the pipe.

3. Apparatus as claimed in claim 1, in which sixteen resonators in two groups of eight are used.

4. Apparatus as claimed in claim 1, in which the electromagnetic radiation is microwave radiation.

5. Apparatus as claimed in claim 1, in which the dissimilar fluids are oil, water and gas.

6. Apparatus for measuring the relative proportions of oil, water and gas within a pipe, comprising: a plurality of coil resonators with different resonant frequencies surrounding the pipe with the pipe passing through the coils of the coil resonators; a variable frequency source of electromagnetic radiation for sending electromagnetic radiation at a plurality of different frequencies into the coil resonators; and an electromagnetic radiation sensor for measuring electromagnetic radiation emitted by each of the coil resonators.

7. Apparatus for measuring the relative proportions of dissimilar fluids within a pipe having an axis, comprising:
a first coil resonator which includes means for providing a first resonant cavity, the pipe passing through the first resonant cavity, and a first coil inside the first resonant cavity and around the pipe, the first coil having an axis which is displaced from the axis of the pipe;
a variable frequency source of electromagnetic radiation for sending electromagnetic radiation into the first coil resonator; and
an electromagnetic radiation sensor for measuring electromagnetic radiation emitted by the first coil resonator.

8. Apparatus as claimed in claims 7, further comprising a second coil resonator which includes means for providing a second resonant cavity, the pipe passing through the second resonant cavity, and a second coil inside the second resonant cavity and around the pipe, the second coil having an axis which is displaced from the axis of the pipe and which is also displaced from the axis of the first coil.

9. Apparatus as claimed in claim 8, wherein the first and second coil resonators have the same natural resonant frequency.

10. Apparatus as claimed in claim 8, wherein the first and second coil resonators have different natural resonant frequencies.

11. Apparatus as claimed in claim 7, wherein the dissimilar fluids are oil, water and gas.

* * * * *